United States Patent [19]
Sohn

[11] Patent Number: 5,387,328
[45] Date of Patent: Feb. 7, 1995

[54] BIO-SENSOR USING ION SENSITIVE FIELD EFFECT TRANSISTOR WITH PLATINUM ELECTRODE

[75] Inventor: Byung-ki Sohn, Daegu, Rep. of Korea

[73] Assignee: Sensor Technology Research Center of Kyungpook National University, Daegu, Rep. of Korea

[21] Appl. No.: 46,751

[22] Filed: Apr. 15, 1993

[30] Foreign Application Priority Data

Jan. 15, 1993 [KR] Rep. of Korea .................. 93-492

[51] Int. Cl.$^6$ ........................................... G01N 27/26
[52] U.S. Cl. .................. 204/403; 204/416; 204/418; 435/288; 435/817
[58] Field of Search .............. 204/403, 416, 418, 419; 435/288, 291, 817

[56] References Cited

U.S. PATENT DOCUMENTS

| | | | |
|---|---|---|---|
| 4,839,000 | 6/1989 | Eddowes | 204/403 |
| 4,894,137 | 1/1990 | Takizawa et al. | 435/817 |
| 4,970,145 | 11/1990 | Bennetto et al. | 204/403 |

*Primary Examiner*—John Niebling
*Assistant Examiner*—Bruce F. Bell
*Attorney, Agent, or Firm*—Birch, Stewart, Kolasch & Birch

[57] ABSTRACT

A bio-sensor employs an ion senstive field effect transistor (ISFET) comprising a source 1 and a drain 3 formed in a substrate, an ion sensitive gate 2 placed between the source 1 and drain 3, an ion sensitive film 4 formed on the ion sensing gate 2, an immobilized enzyme membrane 5 defined on the ion sensitive film 4 and, a Pt electrode 6 formed on the ion sensitive film 4. The sensor has a Pt eleletrode being capable of sensing all biological substances which generate $H_2O_2$ in enzyme reaction, whereby having the high sensitivity and the rapid reaction time.

3 Claims, 2 Drawing Sheets

BIO-SENSOR USING ION SENSITIVE FIELD EFFECT TRANSISTOR WITH PLATINUM ELECTRODE

BACKGROUND OF THE INVENTION

1. Field of the invention

The present invention relates to a bio-sensor using an ion-sensitive field effect transistor (ISFET) which has a platinum(Pt) electrode, which allows extremely to sensing characteristic.

2. Description of the Related Art

Bio-sensors for sensing biological substances are widely employed in the fields of medical diagnosis, fundamental science, food engineering and the like. Typically, conventional bio-sensors include a spectrophotometer or glass electrode, and are disadvantageous in that they are relatively large in size, very expensive and difficult to handle.

Accordingly, many attempts have been made to obtain a bio-sensor to which overcomes the aforementioned disadvantages in the fields of medical diagnosis and food engineering. To satisfactory the aforementioned demand, an ion sensitive FET (ISFET), known as a semiconductor ion sensor, has been proposed.

Since the bio-sensor employing an ISFET is fabricated by the integrated circuit process technology, it has many advantages, such as small size, mass producibility and ease of standardization. As a result, it has been considered that the potential for developing a bio-sensor satisfying the aforementioned demand is very great.

Such a bio-sensor employing an ISFET developed heretofore, however, has small sensitivity and long response time. As a result, it is difficult to employ the bio sensor for practical use.

SUMMARY OF THE INVENTION

Accordingly, an object of the present invention is to provide an improved bio-sensor in which a Pt electrode is employed with an ISFET bio-sensor, whereby the sensitivity performance of the bio-sensor is improved.

To achieve the above object, according to a preferred aspect of the present invention, there is provided a bio-sensor using an ion sensitive field effect transistor (ISFET) comprising:

a source and a drain formed in a substrate;

an ion sensitive gate placed between the source and drain;

an ion sensitive film formed on the surface of the substrate and on the ion sensing gate;

a Pt electrode formed on the ion-sensitive film surrounding the periphery of the ion sensing gate; and an immobilized enzyme formed defined on the ion sensitive including the Pt electrode domain.

The above and other objects, features and advantages of the present invention will be apparent from the following description with reference to the accompanying drawings. However, it should be understood that the detailed description, while indicating preferred embodiments of the invention, is given by way of illustration only, since various changes and modifications within the spirit and scope of the invention will become apparent to those skilled in the art from this detailed description.

BRIEF DESCRIPTION OF THE DRAWINGS

However, it should be understood that the detailed description, while indicating preferred emobidments of the invention, is given by way of illustration only, since various changes and modifications within the spirit and scope of the invention will become apparent to those skilled in the art from this detailed description.

DETAILED DESCRIPTION OF THE INVENTION

A preferred example of the present invention will be now described hereinafter.

Figure 1:
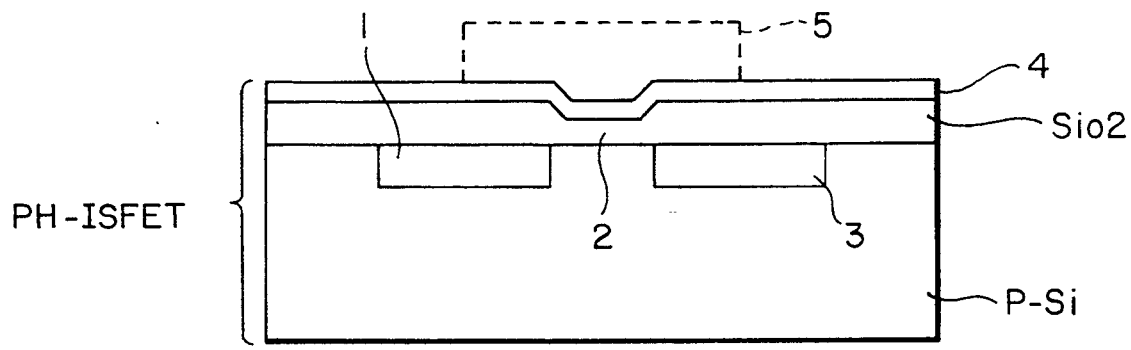
FIG. 1 is a cross-section view of a conventional bio-sensor using an ion sensitive field effect transistor.

FIG. 1 is a cross-section view of an currently used ordinary ISFET bio-sensor. In the drawing, reference numeral 1 denotes a source, 2 denotes an ion sensing gate, 3 denotes a drain, 4 denotes an ion sensitive film and 5 denotes an immobilized enzyme membrane.

In the ISFET bio-sensor shown in FIG. 1, the ion sensitive film 4 is formed on the ion sensing gate 2. The immobilized enzyme membrane is formed on the ion sensitive film 4 and serves to sense specific biological substances.

In FIG. 1, the ISFET is defined by the parts not including the immobilized enzyme membrane.

When the ordinary ISFET bio-sensor shown in FIG. 1 is immersed in a test solution, the immobilized enzyme membrane reacts with the specific biological substance in the test solution. As a result, the ion concentration in the enzyme fixing film 5 will vary in proportion to the concentration of the specific biological substance in the test solution. This above-mentioned variation in ion concentration is sensed by the ISFET, whereby the concentration of the specific biological substance can be measured.

For example, in the case of an ISFET glucose ($\beta$-D-glucose) sensor. When the glucose diffuses into the immobilized enzyme membrane, the enzyme(glucose oxidase) reacts as follows;

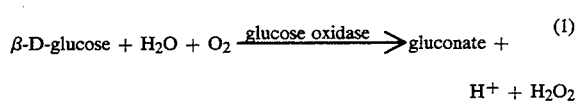

$$\beta\text{-D-glucose} + H_2O + O_2 \xrightarrow{\text{glucose oxidase}} \text{gluconate} + \quad (1)$$

$$H^+ + H_2O_2$$

As shown by the equation (1), hydrogen ions are increased by the reaction of the glucose oxidase, and the increase of the hydrogen ions is sensed by a pH-ISFET, whereby the concentration of the glucose can be measured. But the entire sensitivity of the bio-sensor is small and the response time is undesirably long, since the hydrogen ion has a relatively lower dissociation constant in such a reaction with the enzyme. To overcome these disadvantages of the conventional ISFET bio-sensor, in the present invention; a Pt electrode is proposed.

Figure 2A:
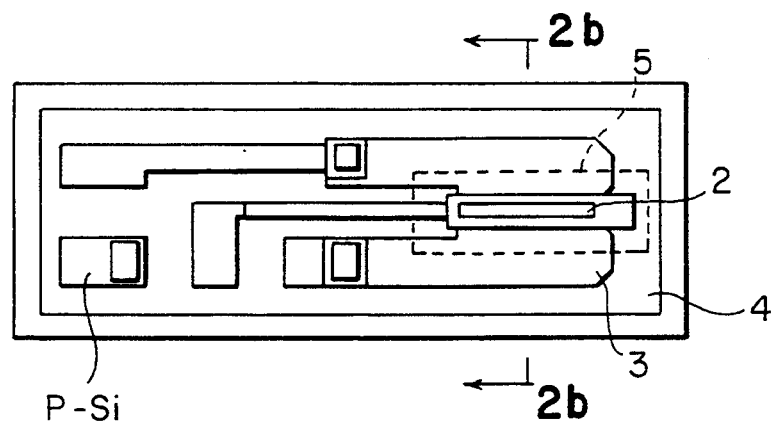
FIGS. 2a and 2b illustrates a bio-sensor using an ion sensitive field effect transistor according to the present invention, in which FIG. (a) is a plan view of the bio-sensor and FIG. (b) is a cross sectional view taken along line A-A' in FIG. 2 (a)
Figure 2B:
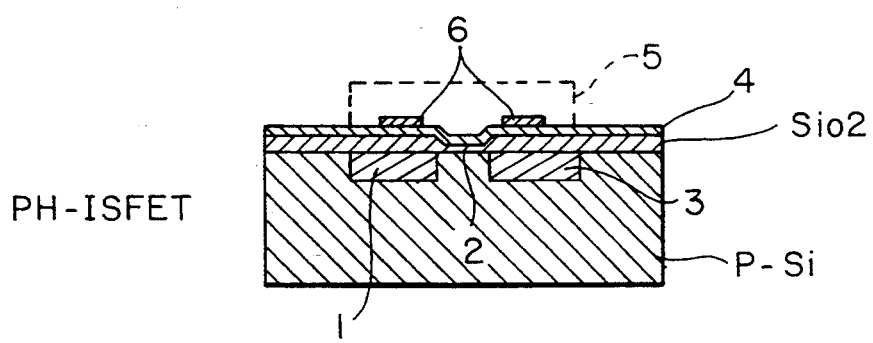

FIG. 2 (b) illustrates a bio-sensor employing an ISFET according to the present invention. A Pt electrode 6 is formed on the ion sensitive film 4 surrounding the periphery of the ion sensing gate (2) and below and in contact with the immobilized enzyme membrane (5), to increase the amount of hydrogen ions generated.

FIG. 2 (a) is a plane view of the bio-sensor according to the present invention and FIG. 2 (b) is a cross-sectional view taken along line A-A' shown in FIG. 2 (a).

With the structure shown in FIG. 2, if 0.7 V higher than a reference voltage(i.e., ground voltage) is applied to the Pt electrode 6, $H_2O_2$ produced as a by-product during the enzyme reaction of the equation (1) is electrolyzed as follows, so that the amount of hydrogen ions is increased.

$$H_2O_2 \xrightarrow{0.7 V} 2H^+ + O_2 + 2e^- \qquad (2)$$

The amount of hydrogen ions increased is sensed by the ISFET and, thus, the sensitivity and response time of the bio-sensor to glucose can be improved.

The Pt electrode 6, in addition to being applicable to the glucose sensor described above, can be employed with any ISFET bio-sensor, such as a lactose sensor, a sucrose sensor or a L-amino acid sensor, which generate $H_2O_2$ during their enzyme reaction.

Each reaction equations of such sensors are as follows.

1. lactose $$\text{lactose} + H_2O \xrightarrow{\beta\text{-galactosidase}} \text{galactose} + \beta\text{-D-glucose} \qquad (A)$$

$$\beta\text{-D-Glucose} + H_2O + O_2 \xrightarrow{\text{glucose oxidase}} \text{gluconate} + H^+ + H_2O_2 \qquad (A')$$

2. sucrose $$\text{sucrose} + O_2 + H_2O \xrightarrow{\text{invertase}} \alpha\text{-D-glucose} \qquad (B)$$

$$\alpha\text{-D-glucose} \xrightarrow{\text{mutarotase}} \beta\text{-D-glucose} \qquad (B')$$

$$\beta\text{-D-glucose} + H_2O + O_2 \xrightarrow{\text{glucose oxidase}} \text{gluconate} + H^+ + H_2O_2 \qquad (B'')$$

3. L-amino acid $$\text{L-amino acid} + O_2 + H_2O \xrightarrow{\text{L-amino oxidase}} \alpha\text{-keto acid} + H_2O_2 + NH_3 \qquad (C)$$

As stated in the above equations 1,2,3, since $H_2O_2$ is generated in the enzyme reaction, the Pt electrode can be preferably employed with each of the respective sensors. Accordingly, $H_2O_2$ is electrolyzed by the reaction represented by the equation 2, and the amount of hydrogen ion generated is greatly increased.

Figure 3:
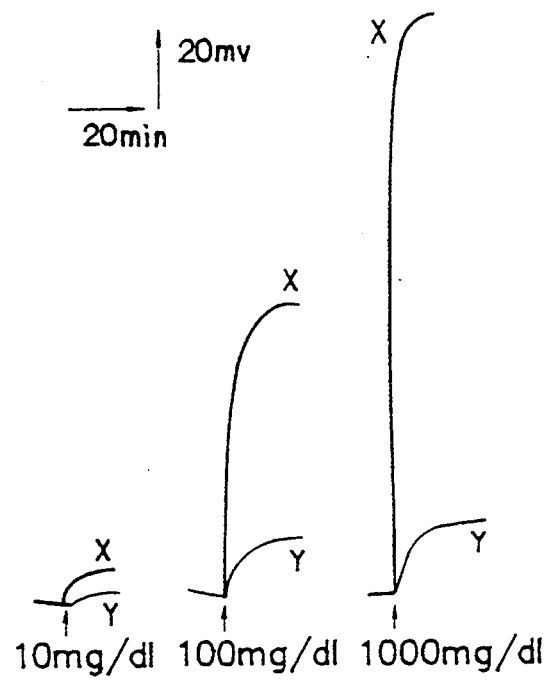
FIG. 3 is a graph comparing time responses of the bio-sensor of the present invention with those of the conventional bio-sensor; and, FIG. 4 is a graph comparing the calibration curve of the present invention with that of the conventional bio-sensor.

FIG. 3 is a graph comparing the response times X of the ISFET glucose sensor having the Pt electrode according to the present invention with those Y of the conventional ISFET glucose sensor without the Pt electrode under conditions of the glucose concentrations of 10 mg/dl, 100 mg/dl and 1000 mg/dl.

Figure 4:
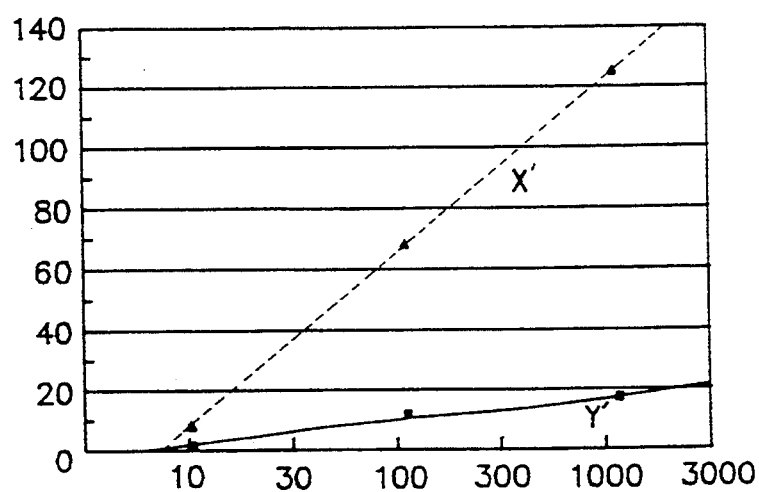

FIG. 4 is a graph comparing the calibration curve X' of the ISFET glucose sensor having the Pt electrode according to the present invention with the calibration curve Y' of the conventional ISFET glucose sensor under the conditions of the concentrations of 10 mg/dl, 100 mg/dl and 1000 mg/dl.

As can be seen from FIGS. 3 and 4, the glucose sensor of the present invention has a superior sensing characteristic to that of the conventional ISFET glucose sensor.

As mentioned above, since the ISFET bio-sensor with a Pt electrode according to the present invention generates about a three-fold increase in hydrogen ions, as compared to the conventional bio-sensor, bio-sensor of the present invention has the advantages of rapid response time as well as high sensitivity.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A bio-sensor employing an ion-sensitive field effect transistor (ISFET) comprising:
   a substrate comprising a source and a drain;
   an ion sensing gate disposed between the source and the drain;
   an ion-sensitive film formed on the surface of the substrate and the ion sensing gate;
   a Pt electrode domain formed on the ion-sensitive film surrounding the periphery of the ion sensing gate; and
   an immobilized enzyme membrane disposed on the ion-sensitive film and the Pt electrode domain.

2. The bio-sensor according to claim 1, wherein said immobilized enzyme membrane is an immobilized glucose oxidase membrane when the bio-sensor is a glucose sensor, a co-immobilized $\beta$-galactosidase and glucose oxidase membrane when the bio-sensor is a lactose sensor, a co-immobilized invertase, mutarotase, and glucose oxidase membrane when the bio-sensor is a sucrose sensor, or an immobilized L-amino acid oxidase membrane when the bio-sensor is an L-amino acid sensor.

3. The bio-sensor according to claim 2, wherein said immobilized enzyme membrane is an immobilized glucose oxidase membrane.

* * * * *